United States Patent [19]

Bronstert

[11] Patent Number: 4,786,736
[45] Date of Patent: Nov. 22, 1988

[54] PREPARATION OF DIAZIRIDINES AND PRODUCTS THEREFROM

[75] Inventor: Klaus Bronstert, Carlsberg, Fed. Rep. of Germany

[73] Assignee: BASF Aktiengesellschaft, Fed. Rep. of Germany

[21] Appl. No.: 22,236

[22] Filed: Mar. 5, 1987

[51] Int. Cl.$^4$ .................. C07D 487/04; C07D 229/02
[52] U.S. Cl. ..................................... 548/369; 548/960
[58] Field of Search ................................ 548/369, 960

[56] References Cited

U.S. PATENT DOCUMENTS 3,666,753  5/1972  Mulders .............................. 548/960

OTHER PUBLICATIONS

Shustou et al., Chem. Abstracts, vol. 105 (1986), entry 171500d.

*Primary Examiner*—Donald G. Daus
*Assistant Examiner*—William A. Teoli, Jr.
*Attorney, Agent, or Firm*—Keil & Weinkauf

[57] ABSTRACT

Process for preparing N,N'-dialkyldiaziridines or bicyclic diaziridines of the general formula I or II:

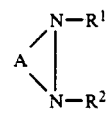

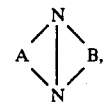

where $R^1$ and $R^2$ are each alkyl or aryl, A is a substituted or unsubstituted one-membered carbon bridge and B is a substituted or unsubstituted three-membered methylene bridge, by reacting a mixture of two moles of a monoamine or one mole of a 1,3-diamine with one mole of an aldehyde or ketone at 25°–70° C., preferably 40°–50° C., while thoroughly mixing with one mole of an aqueous solution of an alkali metal or alkaline earth metal salt of hypochlorous acid and extracting with an organic solvent, preferably chloroform, from the reaction mixture, as well as bicyclic diaziridines which have 1,3-diazabicyclo-[3.1.0]-hexane as basic structure and are prepared using 2,2-dimethyl-1,3-propylenediamine.

3 Claims, No Drawings

PREPARATION OF DIAZIRIDINES AND PRODUCTS THEREFROM

The present invention relates to a process for preparing N,N'-dialkyldiaziridines or bicyclic diaziridines of the general formula I or II:

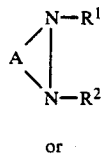

or

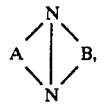

where $R^1$ and $R^2$ are each alkyl or aryl, A is a substituted or unsubstituted one-membered carbon bridge and B is a substituted or unsubstituted three-membered methylene bridge, by reacting an aliphatic monoamine or 1,3-diamine with an aliphatic, cycloaliphatic, aromatic or heterocyclic aldehyde or ketone in the presence of a halogen-containing oxidizing agent.

N,N'-dialkyldiaziridines or bicyclic diaziridines are intermediates for preparing substituted hydrazines [cf. Chem. Ber. 97, (1964), 49–60] are used for equipping polymers with amino end groups (cf. U.S. patent application Ser. No. 889,372). The known processes for their preparation are complicated and material- and energy-intensive, and they give unsatisfactory yields.

For instance, in one prior art process alkylchloramines are first obtained with an excess of amines and are then reacted with separately prepared Schiff's bases. In another process, formaldehyde is first reacted with amines in the presence of a large excess of sodium hydroxide solution and then, at low temperatures, with chlorine bleach liquor (cf. Chem. Ber. 99 (1966), 2104–9). Yields of target products are always appreciably below theory.

It is an object of the present invention to improve the preparation of N,N'-dialkyldiaziridines and bicyclic diaziridines.

We have found that this object is achieved with a process according to the following description and as defined in the appended claims.

In the N,N'-dialkyldiaziridines of the general formula (I) or in the bicyclic diaziridines of the general formula (II)

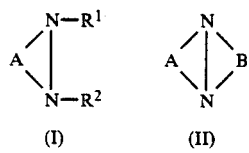

$R^1$ and $R^2$ are each alkyl, in particular $C_1$–$C_6$-alkyl, preferably methyl. A is a substituted or unsubstituted one-membered carbon bridge, preferably methylene of the general formula

where $R^3$ and/or $R^4$ are each hydrogen, $C_1$–$C_4$-alkyl, phenyl or cyclohexyl, or where $R^3$ and $R^4$ together form a ring. B is a substituted or unsubstituted three-membered methylene bridge. Preferably B is —CH$_2$—CH$_2$—CH$_2$ or

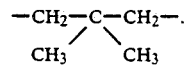

In the process according to the invention, the preferred aldehyde or ketone is formaldehyde, acetaldehyde, isobutyraldehyde, acetone, methyl ethyl ketone or cyclohexane, the preferred amine is an alkylamine of 1 to 6 carbon atoms, the preferred diamine is 1,3-propylenediamine, 2,2-dimethyl-1,3-propylenediamine or 1,3-butylenediamine, and the hypochlorous acid salt used is sodium hypochlorite.

In the process according to the invention, first the monoamine is mixed with an aldehyde or ketone in a molar ratio of 2:1. If a 1,3-alkylenediamine is used, a molar ratio of 1:1 is employed. At 25°–70° C., preferably at 40°–50° C., an aqueous alkali metal or alkaline earth metal hypochlorite solution is then added dropwise with thorough stirring in an amount to give one mole of active chlorine per two moles of starting amine (or one mole of active chlorine per mole of diamine).

The diaziridine formed is then extracted from the reaction solution with a suitable solvent, preferably chloroform, and obtained in the pure form by distillation, preferably under reduced pressure, and, if necessary, subsequent recrystallization. As is not the case with the solvents described in the literature, prior evaporation of the reaction solution or saturation with potassium hydroxide can be dispensed with.

With the process according to the invention it is in particular surprising that the maximum yield is obtained within the range from 40° to 50° C. Under these conditions, the use of additional bases such as amines or alkali metal hydroxides in the synthesis is not necessary. In the literature, by contrast, it is stated that the reaction has to be carried out in a strongly alkaline medium and at low temperatures [cf. Chem. Ber. 99 (1966), 2105, lines 1–9].

The improvement in yield goes hand in hand with the reduction in, or the disappearance of, unwanted resinous byproducts which, in known processes, are precipitated during the reaction and/or, in the distillation of the extracts, remain as residue. The process according to the invention provides for more efficient preparation of diaziridines than known processes.

EXAMPLES 1 AND 2

1. Propylene-1,3-diaziridine (1,5-diazabicyclo[3.1.0-]hexane)

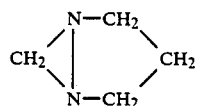

A one-liter four-necked flask is charged with 74 g (1 mol) of 1,3-diaminopropane. 100 g of 30% strength by weight formaldehyde (1 mol) are added dropwise with stirring at 45° C., followed at the same temperature and with very thorough stirring by 548 cm³ (1 mol) of aqueous sodium hypochlorite solution (content 12.5–13.5% by weight of active chlorine). After the mixture has cooled down, it is extracted four times with 700 cm³ of chloroform each time. The chloroform is distilled off under slightly reduced pressure (column bottom temperature about 40° C.). The diaziridine is distilled off at 2 mbar. Boiling point 35°–42° C., crude yield 80 g=95% of theory, purity according to GC* about 95%.

*The gas chromatograms were prepared using a Dani 3800 with flame ionization detector and a fused silica capillary (50 m in length, 0.25 mm in internal diameter) coated with silicone SE 54 (stationary phase).
Injection temperature: 140° C.
Temperature gradient: 60°–280° C.
Rate of heating: 3° C./min
Detector temperature: 350° C.
Carrier gas: $N_2$ The product can be purified to more than 99% (GC) by precision distillation with a high reflux ratio of 1:5 through a column containing V 2 A stainless steel Sulzer packings (internal diameter 50 mm, length about 1 m) to avoid a high pressure loss. The target product has a boiling range of about 42° C. at 2.0 mb. For comparison:

The method of U.S. patent application Ser. No. 889,372, page 8, lines 5 to 18, gives a crude yield of about 53% of theory. The distillation leaves about 30 g of a tacky resinous residue.

2. 2,2-Dimethylpropylene-1,3-diaziridine(1,5-diaza-3,3-dimethylbicyclo[3.1.0.]hexane)

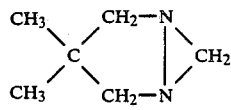

A one-liter four-necked flask is charged with 102 g (1 mol) of 1,3-diamino-2,2-dimethylpropane. 100 g of 30% strength by weight formaldehyde are added dropwise with stirring at 45° C., followed at the same temperature by 548 cm³ of aqueous sodium hypochlorite solution. The mixture is cooled down and then extracted four times with 100 cm³ of chloroform. The chloroform is distilled off under slightly reduced pressure (column bottom temperature 40° C.). The diaziridine is distilled off at 7 mb (boiling point 60°–65° C.). In this vacuum distillation the condenser is cooled with warm water at 38° C. (thermostat) to avoid crystallization of the diaziridine. The receiver is cooled with ice-water, and the bulk of the distillate undergoes crystallization.

Yield about 95% of theory, purity according to GC* 94–95%.

Purification of 2,2-dimethylpropylene-1,3-diaziridine

The cake of crystals obtained after the distillation is mashed with n-pentane under dry nitrogen. After cooling with ice-water, the crystalline mass is suction-filtered off on a glass frit with dry nitrogen. The filter cake is washed three times with icecold pentane and dried with dry nitrogen at room temperature.

By concentrating the mother liquor further crystals can be obtained. All the operations have to be carried out with moisture carefully excluded.

Starting with 968 g of crude material, the following are obtained:

| | |
|---|---|
| 1st crop of crystals = 505 g | purity GC* = 99.4% |
| 2nd crop of crystals = 150 g | purity GC* = 99.5% |
| 3rd crop of crystals = 71 g | purity GC* = 94.3% |

By recrystallizing the 1st crop of crystals from pentane, a diaziridine having a purity of 99.73% (GC*) can be obtained (melting point 38° C.).

The 3rd mother liquor still contains 77% by weight of diaziridine (GC*).

COMPARATIVE EXAMPLES

The 2,2-dimethylpropylene-1,3-diaziridine is prepared as above, except that the reaction temperatures are chosen in accordance with the table. In addition to the crude yield, the amounts of a resin byproduct which is insoluble in the reaction mixture and of resinous distillation residues are determined. In further experiments, the diamine is made to react with the formaldehyde solution in the presence of 2N sodium hydroxide solution. Reaction conditions and yields are shown in the table.

TABLE 1

| Comparative experiment | 2 N NaOH cm³ | Reaction temp °C. | Resins g | Crude yield % by weight of theory |
|---|---|---|---|---|
| 1 | 500 | 5 | 34 | 55.3 |
| 2 | 500 | 10 | 33 | 61.3 |
| 3 | 500 | 25 | 18 | 69.4 |
| 4 | 500 | 45 | 0.5 | 78 |
| 5 | — | 45 | — | 90.4 |
| 6 | — | 60 | 11 | 65 |

EXAMPLES 3–5

In a one-liter four-neck flask, in each case 2 moles of amine or 1 mole of diamine are or is mixed with the aldehydes or ketones (1 mol in each case) indicated in the table at 45° C. with thorough stirring, and 1 mole of aqueous sodium hypochlorite solution is then added at that temperature. The mixture is extracted three times in each case at 20° C. with chloroform, and the resulting diaziridines are isolated by distillation under reduced pressure.

TABLE 2

| Example | Amine | Aldehyde or ketone | Name and formula of diaziridine | Reaction temperature °C. | Yield | Purity by GC* | Boiling point/mb |
|---|---|---|---|---|---|---|---|
| 3 | 1,3-Diamino-propane | i-Butyr-aldehyde | | 45 | 96.8 | 98.3 | 33/0.1 |
| Comparative example | 1,3-Diamino-propane | i-Butyr-aldehyde | | 5 | 72 | 92.8 | 33–37/0.1 |

TABLE 2-continued

| Example | Amine | Aldehyde or ketone | Name and formula of diaziridine | Reaction temperature °C. | Yield | Purity by GC* | Boiling point/mb |
|---|---|---|---|---|---|---|---|
| 4 | 1,3-Diamino-propane | Acetone | 2  | 45 | 77 | 95 | 37–40/0.3 |
| Comparative example | 1,3-Diamino-propane | Acetone | | 5 | 68 | 93 | 37–40/0.3 |
| 5 | n-Butyl-amine | Form-aldehyde | 3  | 45 | 80 | 87 | 44–52/0.5 |
| Comparative example | n-Butyl-amine | Form-aldehyde | | 5 | 51 | 87 | 44–52/0.5 |

1 = s-i-Propyl-1,5-diazabicyclo[3.1.0.]hexane
2 = 6,6-Dimethyl-1,5-diazabicyclo[3.1.0.]hexane
3 = N,N'—Dibutyldiaziridine (cis/trans mixture)
*The gas chromatograms were prepared using a Dani 3800 with flame ionization detector and a fused silica capillary (50 m in length, 0.25 mm in diameter)coated with silicone SE 54 (stationary phase).
Injection temperature: 140° C.
Temperature gradient: 60°–280° C.
Rate of heating: 3° C./min
Detector temperature: 350° C.
Carrier gas: $N_2$

I claim:

1. A process for preparing an N,N'-dialkyldiaziridine or bicyclic diaziridine of the general formula I or II:

$$\begin{array}{c} N-R^1 \\ A \Big| \\ N-R^2 \end{array} \quad (I)$$

or $$\begin{array}{c} N \\ A \Big| B, \\ N \end{array} \quad (II)$$

where $R^1$ and $R^2$ are each alkyl or aryl, A is a substituted or unsubstituted one-membered carbon bridge and B is a substituted or unsubstituted three-membered methylene bridge, by reacting an aliphatic monoamine or 1,3-diamine with an aliphatic, cycloaliphatic, aromatic or heterocyclic aldehyde or ketone in the presence of an oxidizing agent consisting of an aqueous solution of an alkali or alkaline earth metal salt of hypochlorous acid, which consists essentially of reacting a mixture of 2 moles of the monoamine or 1 mole of a 1,3-diamine with one mole of an aldehyde or ketone at a temperature in the range of from 40°–50° C. while thoroughly mixing with 1 mole of said oxidizing agent, extracting the diaziridine formed from the reaction mixture with an organic solvent and finally separating the diaziridine product from said organic solvent by distillation.

2. A process as claimed in claim 1, wherein the hypochlorous acid salt used is sodium hypochlorite.

3. A process as claimed in claim 1, wherein the organic solvent is chloroform.

* * * * *

UNITED STATES PATENT AND TRADEMARK OFFICE
CERTIFICATE OF CORRECTION

PATENT NO. : 4,786,736
DATED : November 22, 1988
INVENTOR(S) : Bronstert

It is certified that error appears in the above-identified patent and that said Letters Patent is hereby corrected as shown below:

ON THE TITLE PAGE,
Add:

(30) Foreign Application Priority Data

March 11, 1986 (DE) Fed Rep. of Germany ... 3607993

Signed and Sealed this

Twenty-third Day of May, 1989

Attest:

DONALD J. QUIGG

*Attesting Officer*  *Commissioner of Patents and Trademarks*